United States Patent

Campbell et al.

[11] Patent Number: 5,323,194
[45] Date of Patent: Jun. 21, 1994

[54] PERIMETER WITH NON SPHERICAL BOWL

[75] Inventors: Charles E. Campbell, Berkeley; Vincent M. Patella, Oakland, both of Calif.

[73] Assignee: Humphrey Instruments Incorporated, San Leandro, Calif.

[21] Appl. No.: 854,550

[22] Filed: Mar. 20, 1992

[51] Int. Cl.[5] .............................................. A61B 3/00
[52] U.S. Cl. ..................................... 351/226; 351/224
[58] Field of Search ............... 351/224, 225, 226, 211, 351/212

[56] References Cited

U.S. PATENT DOCUMENTS 4,561,738 12/1985 Humphrey et al. ................. 351/226

Primary Examiner—William L. Sikes
Assistant Examiner—Hung X. Dang
Attorney, Agent, or Firm—Townsend & Townsend Khourie & Crew

[57] ABSTRACT

A perimeter is disclosed in which the projection surface of the bowl includes a hemispherical section bounded by a cylindrical perimeter to impart to the interior projection surface of the instrument a "bullet shaped" profile. The perimeter of preferred dimension includes a reduced diameter hemisphere occupying the central 45° of solid angle from the fixated patient's eye. The cylindrical perimeter is joined to the hemisphere and is generated about a cylindrical axis commencing at the spherical center of the hemisphere and extending outward normally from the hemisphere to the point of patient eye placement. The diameter of the cylinder matches and forms a projection continuum with the radius of the hemisphere.

24 Claims, 3 Drawing Sheets

PERIMETER WITH NON SPHERICAL BOWL

This invention relates to perimeters. More particularly, a perimeter for the eye is disclosed in which the interior of the bowl perimeter combines a hemisphere with a conic section, preferably a cylinder, to impart to the interior projection surface of the instrument a "bullet shaped" profile. There results reduced instrument dimension and volume to enable placement of the perimeter in a smaller space with no appreciable compromise in the quality of perimetry.

BACKGROUND OF THE INVENTION

Perimetry is the science of testing the field of view of the eye. Such measurements, particularly if they are taken periodically, can be a useful measure of both the health of the eye as well as tool for the tracking of any eye disease.

Conventional perimeters now in use have large hemispherical bowls forming an interior concave projection surface. The patient being examined is faced forward into the concave hemisphere and positioned with the eye to be examined located at the center of the hemisphere. When the eye to be examined is positioned at the center of the hemisphere, the patient is told to fixate at a fixation target located in the center of the projection surface of the hemisphere. When the patient is properly fixated, eye sensitivity is mapped. Typically, mapping occurs through projection of a light stimulus to typically randomly selected locations on the bowl about the fixation point. When these randomly selected locations are observed, aggregated and "mapped", the perimetry of the eye is described.

Projection of the points of light about the fixation point to the interior of the bowl for observation by the patient occurs either statically or dynamically to determine the boundaries of peripheral vision. During static examination, light is projected onto the surface of the bowl with the patient depressing an indicator when the projected light is observed. During dynamic examination, light is projected onto the surface of the bowl at an angle remote from the fixation point and moved towards the patient's central vision adjacent the point of patient fixation with the patient depressing an indicator when the projected light is observed.

In both kinds of perimetry, the location of the spot on the interior projection surface of the instrument must be precisely identified with respect to the solid angle of patient vision with respect to the point of fixation at the time the patient indicates observation of the light. Only when the correlation is precisely made can a definitive and repeatable perimetric examination be made.

In the past, large hemispherical bowls have been used as the inside projection surface of perimeters. These bowls have an internal spherical radius on the order of 30 centimeters—with the result that instrument dimension is large—on the order of at least 60 centimeters wide, 60 centimeters high and at least 30 centimeters depth.

The use of the large hemispherical bowl has advantages. The distance of the eye to any point on the surface of the bowl onto which the light image is projected remains equidistant from the eye. Further, such bowls lend themselves to having a uniformly illuminated background light projected onto their surface. Finally, determining the angle of projection with respect to point of fixation is a straight forward calculation which readily transfers to the desired perimetric measurement and map.

Unfortunately, the size of such bowls constitutes a serious practical problem. Not only must a rather large instrument be fabricated and shipped, but the same instrument in use has practical difficulties. For example, it is common for such instruments to occupy their own room—or portion of a room. The instrument cannot conveniently be moved. Further, when perimetric measurements are taken, the patient almost always comes to the perimeter—perimetric apparatus is never moved to the patient.

SUMMARY OF THE INVENTION

A perimeter is disclosed in which the projection surface of the bowl includes a hemispherical section bounded by a conic perimeter, preferably a cylinder, to impart to the interior projection surface of the instrument a "bullet shaped" profile. The perimeter of preferred dimension includes a reduced diameter hemisphere occupying the central 45° of solid angle from the fixated patient's eye. The cylindrical perimeter is joined to the hemisphere and is generated about a cylindrical axis commencing at the spherical center of the hemisphere and extending outward normally from the hemisphere to the point of patient eye placement. The diameter of the cylinder matches and forms a projection continuum with the radius of the hemisphere. Dimension is important. The hemispherical portion and the cylinder both have a preferred radius of 17.5 centimeters with a range of 15 to 20 centimeters being acceptable. The length of the cylinder from the center of the hemisphere is a preferred 12.5 centimeters with a range of 8 to 16 centimeters being acceptable. The patient's eye is placed on the axis of the cylinder at the end of the cylindrical axis remote from the hemisphere. Projection occurs from a projector typically intruding through the cylinder section of the bowl at an off cylindrical axis position. Projection of the test image occurs to any desired projection location with respected to the fixated patient eye for either static or dynamic testing. During perimetry, and using the computable surfaced coordinates of the combined hemisphere and cylinder, coordinate transformation is made to the hemispherical equivalent of the prior art large hemispherical bowl. With the preferred dimension hemisphere and cylinder, required dioptric shift over the central 30° solid angle of vision is no more than ⅜ths of a diopter as compared to a large hemisphere, an accommodation range of no appreciable consequence for perimetric testing. Required projections beyond the central 30° of solid angle of the eye are subject to large astigmatic aberration in any subject and variations in resultant dioptric accommodation have not been found to be a factor. There results a substantially more compact instrument occupying about ⅛ the volume of the original instrument.

As will become more apparent in the following specification, we illustrate the preferred embodiment using a hemisphere combined with a cylinder to generate the "bullet shaped" projection profile of this invention. Other surfaces can achieve the same result. For example, a paraboloid or an ellipsoid could as well be used—surfaces formed by the rotation of parabolas and ellipses.

It should be also remembered that the term "hemisphere" and "cylinder" are likewise not to be strictly construed. For example, conic sections—of which a cylinder is a specie—can be used. Likewise, departures from spheres can as well be used -so long as the overall resulting shape includes the "bullet shaped" profile.

DESCRIPTION OF THE PREFERRED EMBODIMENT

Figure 1:
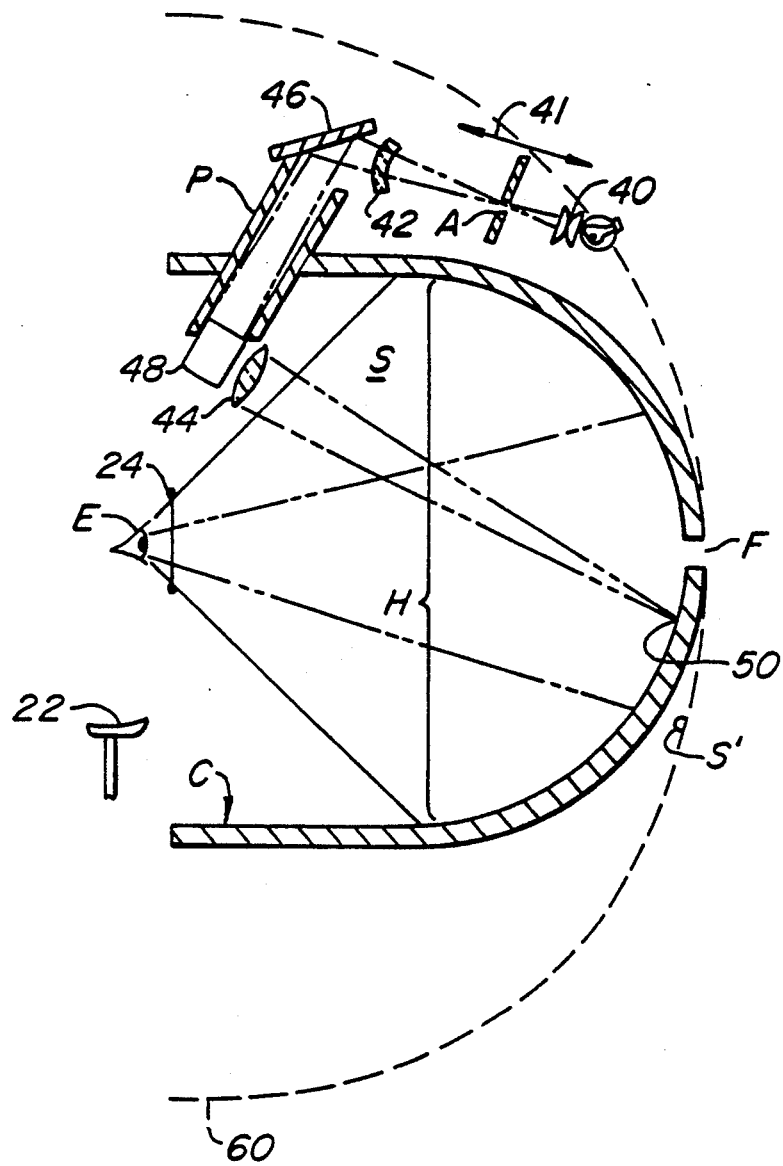
FIG 1 is a side elevation section taken through the hemisphere center and cylindrical axis at the projector with the dimensions of a prior art instrument being shown in broken lines so that both a size comparison and the required accommodation for the central 30° of solid angle may be seen and understood; and, FIG. 2 is a perspective view of the interior projection surface only of the perimeter of this invention illustrating the generally "bullet shaped" profile of the preferred dimension, the off axis projector and the placement of the patient with respect to the instrument for the perimetric test of an eye of the patient.
Figure 2:
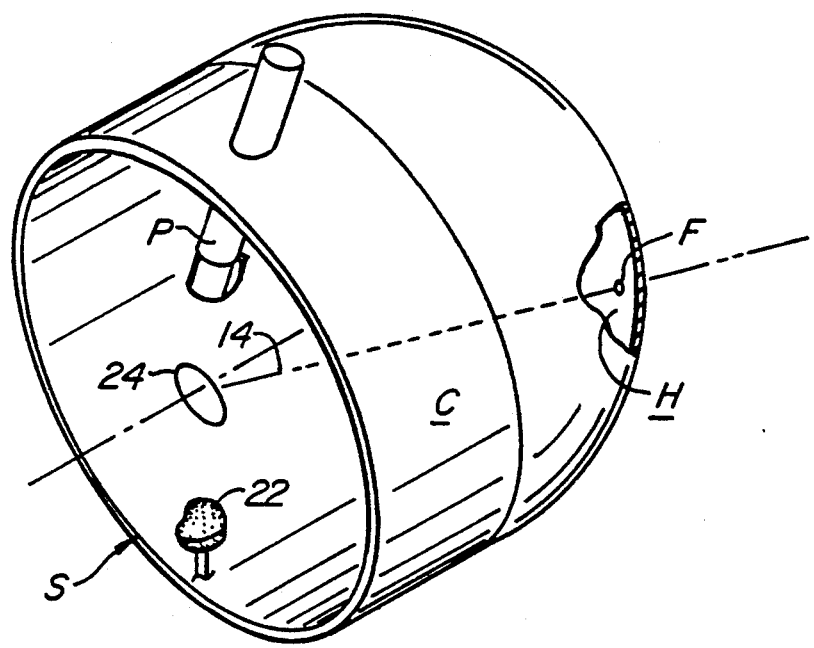

Referring to FIG. 1, the bullet shaped projection surface S is illustrated. In accordance with the embodiment, a hemisphere H is illustrated. In the preferred embodiment, this hemisphere has a radius of 17.5 centimeters; ranges of the radius may vary within the acceptable limits of 15 to 20 centimeters.

Attached to the periphery of the hemisphere H and forming a projection continuum on the interior bowl surface is a cylinder C. Cylinder C has a radius also of 17.5 centimeters with a height of 12.5 centimeters. The radius of the cylinder may vary as the radius of the sphere. Further, a conic section can be used of which the illustrated right angle cylinder is a special—in this case preferred—case.

A projector P is utilized and preferably penetrates cylinder C on an off axis location. This projector is a standard item of manufacture available with that product known as the Humphrey Field Analyzer, a product of Humphrey Instruments of San Leandro, Calif.

Centrally of bullet shaped screen S, there is placed a fixation light F. This fixation light is located on the central radius 16 of hemisphere H and forms a continuously straight line with axis 14 of cylinder C.

At the end of axis 14 of cylinder C there is place a patient observation station. Patient observation station includes a chin rest 22 and a trial frame 24 into which any required prescription of the patient is inserted—typically for examining perimetry within 30° of solid angle of the axis 14, 16 from the patient viewing station to and towards fixation light F.

Referring to FIG. 1, operation of the projector P can be understood. Typically, projector P—known in the prior art Humphrey U.S. Pat. No. 4,561,738—rotates to any desired bowl location from its point of off axis projection. Utilizing the standard surface descriptions for the sphere and cylinder here shown, together with appropriate coordinate transforms to adjust for the off axis location of projection, the distance from the end of the projector P to the particular surface S of the interior of the bullet shaped bowl is computed. An aperture A moves parallel to vector 41 towards and away from lamp L. The aperture A in conjunction with lenses 42, 44 image a stimulus 50 at a random location interior of screen S. Since the angle of stimulus 50 with respect to fixation F is known, the distance from projector P to the particular stimulus point 50 can be computed and aperture A moved to create an image at that location.

Operation of the perimeter is conventional. The patient has either the left or right eye E placed at the patient observation station. The patient is told to fixate on fixation source F. Thereafter, stimulus 50 is randomly moved to locations on bullet shaped projection surface S. By mapping patient response—typically input through an indicator not shown—a perimetric map of eye sensitivity is generated.

Some further comment about the preferred embodiment of this invention can be made. Referring to FIG. 1, and shown in broken lines 60 is a conventional perimeter hemisphere. Several observations can be made.

First, it will be noted that over the central 30° of solid angle of eye E that the departure of surface S of bullet shaped bowl is minor from the surface S' of a sphere. This being the case, it has been determined that no more than ⅜ths of a diopter accommodation is required for in focus viewing of stimulus 50 within this solid angle. Such required accommodation is not significant in a perimetric examination.

Secondly, the sphere occupies 45° of solid angle with respect to eye E. Thereafter, the cylinder is utilized.

Thirdly, it will be understood that perimetric vision beyond 30° of solid angle has at least two limitations. First, and because of the practical solid angle of vision correction provided by trial frames 24, the frames (together with any inserted corrective prescription) are removed. Secondly, such peripheral vision is subject to high degrees of astigmatism—even with those having "perfect" (emmetropic) vision. Consequently, correction of the eye's vision is not required—only measurement of perimetric sensitivity need occur.

It will be understood that the dimension reduction realized by this invention is substantial. First, prior art hemispherical perimeters are enclosed in housings which are rectilinear. Thus, the conventional perimeter housing is at least 30 centimeters of depth and has a 60 by 60 centimeter dimension addressed to the patient. As contrasted to this dimension, the present invention can be contained in a package having a depth of 30 centimeters with a 35 by 35 centimeter dimension addressed to the patient. Consequently, the perimeter of this invention can occupy a total volume that is ⅓ of that volume occupied by a conventional perimeter.

Figure 3A:
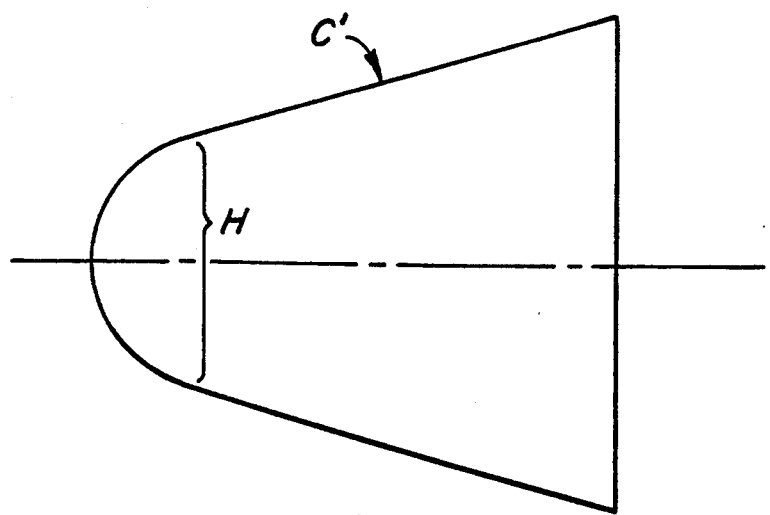
FIGS. 3A, 3B and 3C are respective alternate embodiments of the "bullet shaped" profile with FIG. 3A illustrating a portion of a hemisphere combined with a conic section, FIG. 3B illustrating and ellipsoid shape truncated at the viewing station, and FIG. 3C illustrating a paraboloid.
Figure 3B:
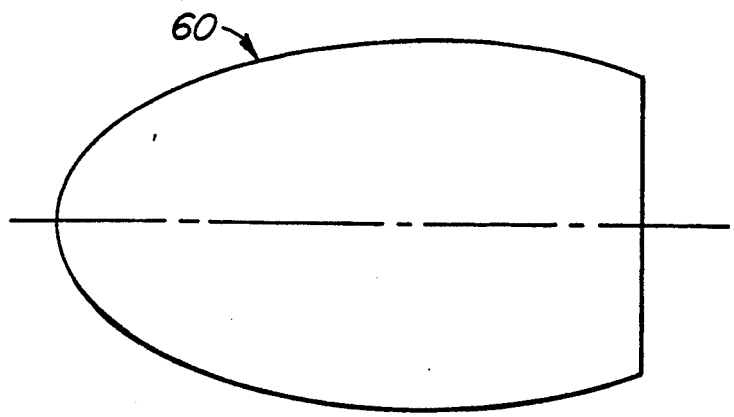
Figure 3C:
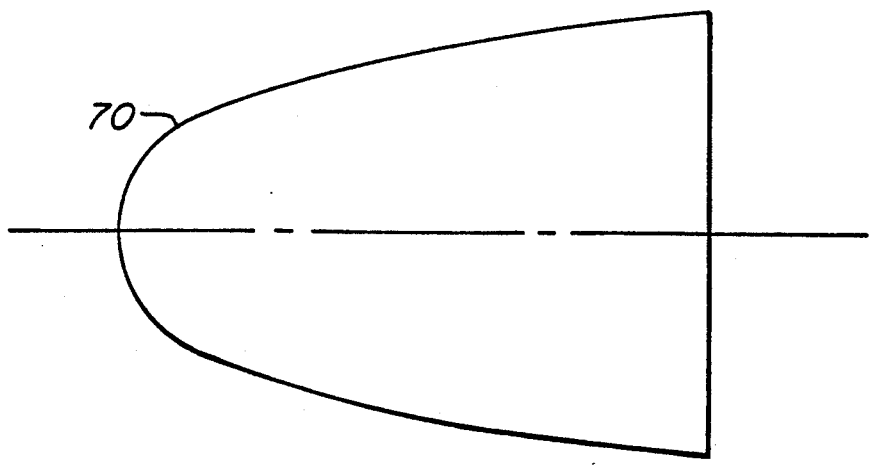

Referring to FIGS. 3A-3C, it will be seen that other shapes can also be utilized. Referring to FIG. 3A, a portion of a hemisphere H is combined with a conic section C'—the conic section here being shown with an apex adjoined to form the desired projection continuum with the portion of the hemisphere. Observing FIG. 3B, a projection surface is shown which includes an ellipsoid. The ellipsoid is truncated in the vicinity of one of its foci to form the opening for the patient observation station. Finally, and in FIG. 3C, a paraboloid is illustrated.

Observing all three FIGS. 3A-3B, at least three common characteristics can be observed, which characteristics are shared by the preferred embodiment. First, each surface forms for the central 30° of vision a surface which is capable of approximating a sphere. Preferably, the surfaces do not depart from the spherical to an extent that will require more than ½ diopter of accommodation in the central 30° of solid angle of vision. Secondly, the interior of all surfaces forms a continuum for the projection of the image of the stimulus 50. Finally, all of the illustrated profiles project to a "bullet shaped" profile enabling the reduction of perimeter dimension which is characteristic of this invention.

What is claimed is:

1. A perimeter comprising in combination:

an observing station having a point for placement of a patient's eye;

a fixation target for enabling a patient with an eye at said observing station to fixate on said fixation target whereby said eye of said patient is aligned with respect to said fixation target;

a bowl having a concave interior directed toward said observing station with an open end adjacent said observing station for providing a continuum onto which light stimuli can be projected; and, a projector for projecting to said bowl at locations on said concave interior of said bowl light stimuli for observation by the peripheral vision sensitivity of the fixated eye of said patient whereby the perimetry of said eye of said patient can be mapped;

the improvement in the shape of said bowl comprising in combination:

said bowl having a substantially elongate shaped interior projection profile symmetrical about a major axis between said fixation target and said observing station at said open end of said bowl;

said concave interior forming an interior continuum for the projection of images to stimuli for observation by an eye at said observation station fixated on said fixation target; and said concave interior in the central 30° of solid angle of vision imposing no more than $\frac{1}{2}$ diopter of blur for viewing said stimuli within said 30° solid angle of vision.

2. The invention of claim 1 and wherein said bowl having a concave interior includes:

a first hemispherical section symmetrical about an axis defining a concavity directed toward said patient; and, said bowl having a second inside section symmetrical about said axis joined to said hemispherical section and forming a projection continuum with said hemispherical section.

3. The perimeter of claim 2 and wherein said second inside section of said perimeter is cylindrical.

4. The perimeter of claim 2 and wherein said hemispherical section of said bowl defines a radius to said sphere ranging from 15 to 20 centimeters.

5. The perimeter of claim 4 and where said hemispherical section has a length in the range of 8 to 16 centimeters.

6. The perimeter of claim 2 and wherein said hemispherical section of said bowl defines a radius to said sphere of 17.5 centimeters.

7. The perimeter of claim 6 and wherein said second inside section is cylindrical and has a length of 12.5 centimeters.

8. The perimeter of claim 2 and where said projector protrudes off said axis of said concave interior of said bowl for the projection of images to said bowl.

9. A perimeter comprising in combination:

an observing station having a point for placement of a patient's eye;

a fixation target for enabling a patient with an eye at said observing station to fixate on said fixation target whereby said eye of said patient is aligned with respect to said fixation target;

a bowl having a concave interior directed toward said patient and an open end adjacent said observing station; and a projector for projecting to said bowl at locations on said concave interior of said bowl light for observation by the peripheral vision sensitivity of the fixated eye of said patient whereby the perimetry of said eye of said patient can be mapped;

said bowl having a substantially elongate shaped interior projection profile symmetrical about a major axis between said fixation target and said observing station at said open end of said bowl;

said concave interior forming an interior continuum for the projection of images to stimuli for observation by an eye at said observation station fixated on said fixation target;

said concave interior in the central 30° of solid angle of vision imposing no more than $\frac{1}{2}$ diopter of blur for viewing stimuli within said 30° of solid angle of vision.

10. The invention of claim 9 and where in said concave interior includes an ellipsoid.

11. The invention of claim 9 and where in said concave interior includes a paraboloid.

12. The invention of claim 9 and wherein said bowl at said concave interior includes:

a first hemispherical section defining a concavity directed toward said patient; and said bowl having a second inside section joined to said hemispherical section and forming a projection continuum with said hemispherical section.

13. The perimeter of claim 12 and wherein said hemispherical section of said perimeter subtends a solid angle of about 45° with respect to said observing station having said patient's eye.

14. The perimeter of claim 12 and wherein said hemispherical section of said bowl defines a radius to said sphere ranging from 15 to 20 centimeters and where said second inside section has a length in the range of 8 to 16 centimeters.

15. A perimeter comprising in combination:

an observing station having a point for placement of a patient's eye;

a fixation target for enabling a patient with an eye at said observing station to fixate on said fixation target whereby said eye of said patient is aligned with respect to said fixation target;

a bowl having a concave interior directed toward said observing station with an open end adjacent said observing station for providing a continuum onto which light stimuli can be projected; and, a projector for projecting to said bowl at locations on said concave interior of said bowl light stimuli for observation by the peripheral vision sensitivity of the fixated eye of said patient whereby the perimetry of said eye of said patient can be mapped;

the improvement in the shape of said bowl comprising in combination:

said bowl having a substantially elongate shaped interior projection profile symmetrical about a major axis between said fixation target and said observing station at said open end of said bowl;

said concave interior forming an interior continuum for the projection of images to stimuli for observing by an eye at said observation station fixated on said fixation target; and, a first substantially hemispherical section defining a concavity directed toward said patient; and, said bowl having a second inside section joined to said hemispherical section and forming a projection continuum with said hemispherical section.

16. The invention of claim 15 and wherein:
said concave interior in the central 30° of solid angle of vision imposing no more than ½ diopter of blur for viewing said stimuli within said 30° solid angle of vision.

17. The perimeter of claim 15 and wherein said second inside section of said perimeter is cylindrical.

18. The perimeter of claim 15 and wherein said substantially hemispherical section of said bowl defines a radius to said sphere ranging from 15 to 20 centimeters.

19. The perimeter of claim 15 and wherein said substantially hemispherical section of said bowl defines a radius to said sphere of 17.5 centimeters.

20. The perimeter of claim 19 and where said second inside section has a length in the range of 8 to 16 centimeters.

21. The perimeter of claim 20 and wherein said second inside section is cylindrical and has a length of 12.5 centimeters.

22. The perimeter of claim 15 and where said projector protrudes off said major axis of said bowl for the projection of images to said bowl.

23. The perimeter of claim 15 and where said substantially hemispheric section and said substantially conic section combine to form an elliptical section.

24. The perimeter of claim 15 and where said substantially hemispherical section and said substantially conic section combine for form a parabolic section.

* * * * *